US008868159B2

(12) United States Patent
Onimura

(10) Patent No.: US 8,868,159 B2
(45) Date of Patent: Oct. 21, 2014

(54) OPTICAL IMAGING DIAGNOSTIC APPARATUS AND THE DISPLAY CONTROL METHOD THEREOF

(75) Inventor: Yuuji Onimura, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 711 days.

(21) Appl. No.: 13/075,943

(22) Filed: Mar. 30, 2011

(65) Prior Publication Data

US 2011/0245684 A1   Oct. 6, 2011

(30) Foreign Application Priority Data

Mar. 30, 2010   (JP) ................ 2010-078606

(51) Int. Cl.
- A61B 6/00  (2006.01)
- A61B 5/02  (2006.01)
- A61B 5/00  (2006.01)

(52) U.S. Cl.
CPC ........... *A61B 5/6852* (2013.01); *A61B 5/02007* (2013.01); *A61B 5/0066* (2013.01)
USPC ............ 600/476; 600/477; 600/478; 356/479

(58) Field of Classification Search
None
See application file for complete search history.

(56) References Cited

U.S. PATENT DOCUMENTS

| | | | |
|---|---|---|---|
| 5,383,467 A | 1/1995 | Auer et al. | |
| 8,108,032 B2 | 1/2012 | Onimura et al. | |
| 2009/0306520 A1* | 12/2009 | Schmitt et al. | 600/476 |

FOREIGN PATENT DOCUMENTS

| | | |
|---|---|---|
| EP | 2 062 526 A1 | 5/2009 |
| JP | 2001-079007 A | 3/2001 |
| JP | 2009-128074 A | 6/2009 |
| WO | 2008/044539 A1 | 4/2008 |
| WO | 2009/149131 A1 | 12/2009 |

OTHER PUBLICATIONS

European Extended Search Report dated Jul. 6, 2011 issued in the corresponding European Patent Application No. 11160203.3-1265.
Esenaliev et al, R.O., "Accurate Measurement of Total Attenuation Coefficient of Thin Tissue With Optical Coherence Tomography", IEEE Journal of Selected Topics in Quantum Electronics, IEEE Service Center, Piscataway, New Jersey, US, vol. 9, No. 2, Mar. 1, 2003, pp. 210-221, XP011102887, ISSN:1077-260X, DOT:10.1109/JSTQE.2003.814194.

* cited by examiner

*Primary Examiner* — Long V Le
*Assistant Examiner* — Farshad Negarestan
(74) *Attorney, Agent, or Firm* — Buchanan Ingersoll & Rooney PC

(57) ABSTRACT

An optical imaging diagnostic apparatus including: a designating unit for designating a predetermined circumferential-direction position at the circumference of the transmitting and receiving unit on the cross-sectional image displayed; an extraction unit for extracting, within the plurality of line data used for the generation of the cross-sectional image, line data corresponding to circumferential-direction position designated in the designating unit from the storage unit; a calculation unit for calculating attenuation rate in a predetermined region in a radial direction of a body lumen with respect to the extracted line data; and a display unit for displaying the calculated attenuation rate.

7 Claims, 9 Drawing Sheets

OPTICAL IMAGING DIAGNOSTIC APPARATUS AND THE DISPLAY CONTROL METHOD THEREOF

This application contains subject matter disclosed in, and claims priority to, Japanese Patent Application No. 2010-078606 filed in the Japanese Patent Office on Mar. 30, 2010, the entire content of which is incorporated herein by reference.

TECHNOLOGICAL FIELD

The present invention generally relates to an optical imaging diagnostic apparatus and a display control method.

BACKGROUND DISCUSSION

In the past, there has been used an optical coherent tomography (OCT) apparatus, an example of which is disclosed in Japanese Unexamined Patent Publication No. 2001-79007, and an optical frequency domain imaging (OFDI) apparatus utilizing wavelength sweep, which is an improvement type of apparatus for diagnosing arterioscleosis, for a diagnosis before operation at the time of treatment inside a blood vessel depending on a high functional catheter such as a balloon catheter, a stent and the like, or for a result confirmation after operation Hereinafter, in the present specification, the optical coherent tomography (OCT) apparatus and the optical frequency domain imaging (OFDI) apparatus utilizing wavelength sweep are generically referred to as "optical imaging diagnostic apparatus".

In the optical imaging diagnostic apparatus, an optical probe unit inserted with an imaging core which is attached with an optical lens and an optical mirror (transmitting and receiving unit) at a distal end of an optical fiber is inserted into a blood vessel, and a radial scan in a blood vessel is carried out by emitting a measurement light into the blood vessel from the transmitting and receiving unit at the distal end while rotating the imaging core and concurrently, by receiving a reflected light from a biological tissue. Then, a coherent light is produced by making the light-received reflected light and a reference light interfere with each other, and a cross-sectional image of the blood vessel is derived based on the coherent light.

Generally, in order to carry out a diagnosis by using a measurement result in such an optical imaging diagnostic apparatus, it is preferable for a user, based on the measurement result, to be able to accurately comprehend the morphological feature of the biological tissues inside the blood vessel and the scattering intensity and the absorption level of the measurement light in each biological tissue.

On the other hand, with respect to the blood vessel cross-sectional image drawn out by a B mode in the optical imaging diagnostic apparatus in the present situation, scattering intensity is expressed as pixel intensity, so that it is possible for a user to comprehend the morphological feature of the biological tissue based on the intensity distribution of the pixel. Also, it is possible to comprehend the scattering intensity of the measurement light in each biological tissue based on the intensity value of the pixel. In addition, in case of an optical imaging diagnostic apparatus, it is possible to draw out a blood vessel cross-sectional image of high resolution, so that it is also possible to distinguish between, for example, tunica intima, tunica media, and tunica adventitia, and further, to identify a plaque or the like.

However, in the case of a blood vessel cross-sectional image developed or generated by the B mode, with respect to the biological tissue which is a biological tissue in which scattering intensity of a calcific plaque, a lipid or the like is low and for which it is necessary to make identification depending on the difference of the absorption level of the measurement light, a situation can arise in which it is difficult to properly identify. On the other hand, in the past, there has been proposed a method in which identification is made based on the sharpness of the intensity change of the pixel in the boundary area of the biological tissues, but in case of a biological tissues in which characteristics of the tissue are mixed up, it sometimes happens even for a well trained expert to make a mistake in the identification by only depending on the method. Consequently, in the optical imaging diagnostic apparatus, there has been desired an improvement of the identification performance with respect to a biological tissue in which it is necessary to make identification depending on the difference of the absorption level.

SUMMARY

The an optical imaging diagnostic apparatus and method here make it possible for each biological tissue constituting the generated blood vessel cross-sectional image to be identified based on the difference of the absorption level of the measurement light.

The optical imaging diagnostic apparatus preferably includes a probe having a transmitting and receiving unit for carrying out continuous transmitting of light which is reflected from biological tissue and received as obtained reflected light by the transmitting and receiving unit, with the transmitting and receiving unit being axially movable inside a body lumen while also rotating the transmitting and receiving unit, to generate a plurality of cross-sectional images in an axial direction of the biological tissue using line data of coherent light produced by interference between the obtained reflected light and reference light, with the cross-sectional images being displayed. The optical imaging diagnostic apparatus comprises: designating means for designating a predetermined circumferential-direction position at a circumference of the transmitting and receiving unit on the displayed cross-sectional image; extraction means for extracting, from amongst a plurality of the line data used to generate the cross-sectional image and which is stored in a storage unit, the line data corresponding to the circumferential-direction position designated by the designating means; calculation means for calculating attenuation rate in a predetermined region in a radial direction of the body lumen with respect to the extracted line data; and a display which displays the calculated attenuation rate and the cross-sectional image.

According to another aspect, the optical imaging diagnostic apparatus is provided with the probe including the transmitting and receiving unit for carrying out continuous transmitting of light which is reflected from biological tissue and received as obtained reflected light by the transmitting and receiving unit, with the transmitting and receiving unit being axially movable inside a body lumen while also rotating the transmitting and receiving unit, to generate a plurality of cross-sectional images in an axial direction of the biological tissue using line data of coherent light produced by interference between the obtained reflected light and reference light. The optical imaging diagnostic apparatus comprises: a display; display control means for controlling the display to display the cross-sectional image as a displayed cross-sectional image; a storage unit in which is stored a plurality of the line data including the line data used to generate the displayed cross-sectional image; designating means for designating, on the displayed cross-sectional image, a circumferential-direction position on a circumference of the transmitting and receiving unit; extraction means for extracting, from amongst the plurality of the line data stored in the storage unit, the line data corresponding to the circumferential-direction position designated by the designating means; calculation means for calculating an attenuation rate in a predetermined region in a radial direction of the body lumen with respect to the extracted line data extracted by the extraction means; and the display control means controlling the display to display the calculated attenuation rate calculated by the calculation means.

Another aspect of the disclosure here involves a display control method of an optical imaging diagnostic apparatus, which apparatus comprises a probe including a transmitting and receiving unit for carrying out continuous transmitting of light which is reflected from biological tissue and received as obtained reflected light by the transmitting and receiving unit, with the transmitting and receiving unit being axially movable inside a body lumen while also rotating the transmitting and receiving unit, to generate a plurality of cross-sectional images in an axial direction of the biological tissue using line data of coherent light produced by interference between the obtained reflected light and reference light, with the cross-sectional images being displayed. The control method comprises: designating a predetermined circumferential-direction position at a circumference of the transmitting and receiving unit on displayed cross-sectional image; extracting, from the line data used to generate the cross-sectional image, line data corresponding to the designated predetermined circumferential-direction position; calculating an attenuation rate in a predetermined region in a radial direction of the body lumen with respect to the extracted line data; and displaying the calculated attenuation rate.

The optical imaging diagnostic apparatus and display control method here make it possible to identify respective biological tissues, constituting the displayed blood vessel cross-sectional images which have been generated or developed, based on the differences of absorption levels of the measurement light.

DETAILED DESCRIPTION

Set forth below is a description of an embodiment of the optical imaging diagnostic apparatus disclosed here by way of example. The optical imaging diagnostic apparatus makes it possible to identify respective biological tissues which constitute the drawn-out (generated) blood vessel cross-sectional image based on the difference of the absorption level of the measurement light, and the absorption level of the measurement light in each biological tissue is visualized, and so it is possible for a user to comprehend the difference of the absorption level accurately.

The optical imaging diagnostic apparatus is preferably configured to calculate and display the change of the scattering intensity in the emission direction (that is, the radial direction of the blood vessel) for each biological tissue in a case in which a measurement light is emitted from a transmitting and receiving unit. Here, the change of the scattering intensity in the radial direction for each biological tissue is equivalent to the attenuation rate of the coherent-light intensity (that is, line data) in the radial direction. Consequently, in each embodiment discussed below, the optical imaging diagnostic apparatus is configured such that the attenuation rate in a predetermined region in the radial direction of the line data is calculated and displayed.

By virtue of this, it is possible for a user to comprehend the absorption level of the measurement light in each biological tissue quantitatively as an attenuation rate of a predetermined region in the line data, so that it becomes possible to relatively accurately carry out the identification of each biological tissue based on the difference of the absorption level.

Set forth below is a discussion of details of respective embodiments of the optical imaging diagnostic apparatus and method disclosed as examples here, with reference to the accompanying drawings.

First Embodiment

1. Overall Construction of Imaging Diagnostic Apparatus s

Figure 1:
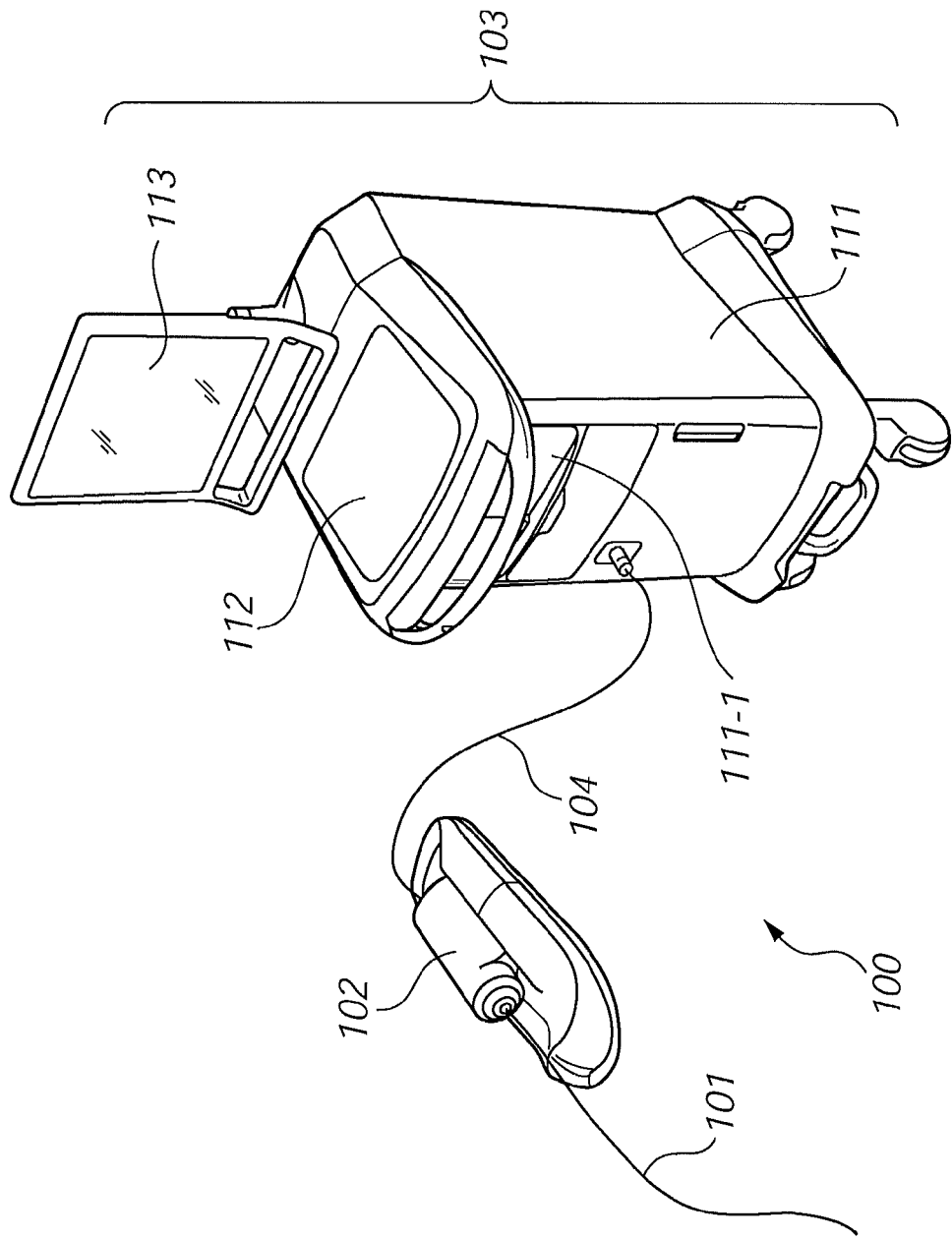
FIG. 1 is a perspective view of an example of an imaging diagnostic apparatus disclosed here.

FIG. 1 presents an external-appearance of an optical imaging diagnostic apparatus (optical coherent tomography apparatus or optical frequency domain imaging apparatus utilizing wavelength sweep) 100 disclosed here according to a first embodiment.

As shown in FIG. 1, the optical imaging diagnostic apparatus 100 is provided with an optical probe unit 101, a scanner & pull-back unit 102 and a steering control apparatus 103. The scanner & pull-back unit 102 and the steering control apparatus 103 are connected by a signal line 104.

The optical probe unit 101 is inserted directly inside a body lumen of a blood vessel or the like and transmits the transmitted measurement light continuously to a biological tissue and concurrently, includes an imaging core provided with a transmitting and receiving unit for receiving the reflected light from the biological tissue continuously, and a state of the biological tissue is measured by using the imaging core. The scanner & pull-back unit 102 is constructed such that the optical probe unit 101 is attachable and detachable, and defines a radial operation of the imaging core inserted in the optical probe unit 101 depending on the driving operation of the installed motor.

The steering control apparatus 103 is configured so that, during operation when carrying out measurements, various kinds of setting values can be inputted. The steering control apparatus 103 also operates to process data obtained by the measurement and to display it as a blood vessel cross-sectional image.

The steering control apparatus 103 includes a main body control unit 111 which processes the data obtained by the measurement and outputs the processed result. A reference numeral 111-1 indicates a printer & DVD recorder which prints out the processed result in the main body control unit 111 and stores it as data signals.

An operation panel 112 allows a user to input various kinds of setting values and instruction. A reference numeral 113 indicates an LCD monitor as a display apparatus and it displays the processed result in the main body control unit 111.

2. Features and Construction of Optical Coherent Tomography Apparatus

Figure 2:
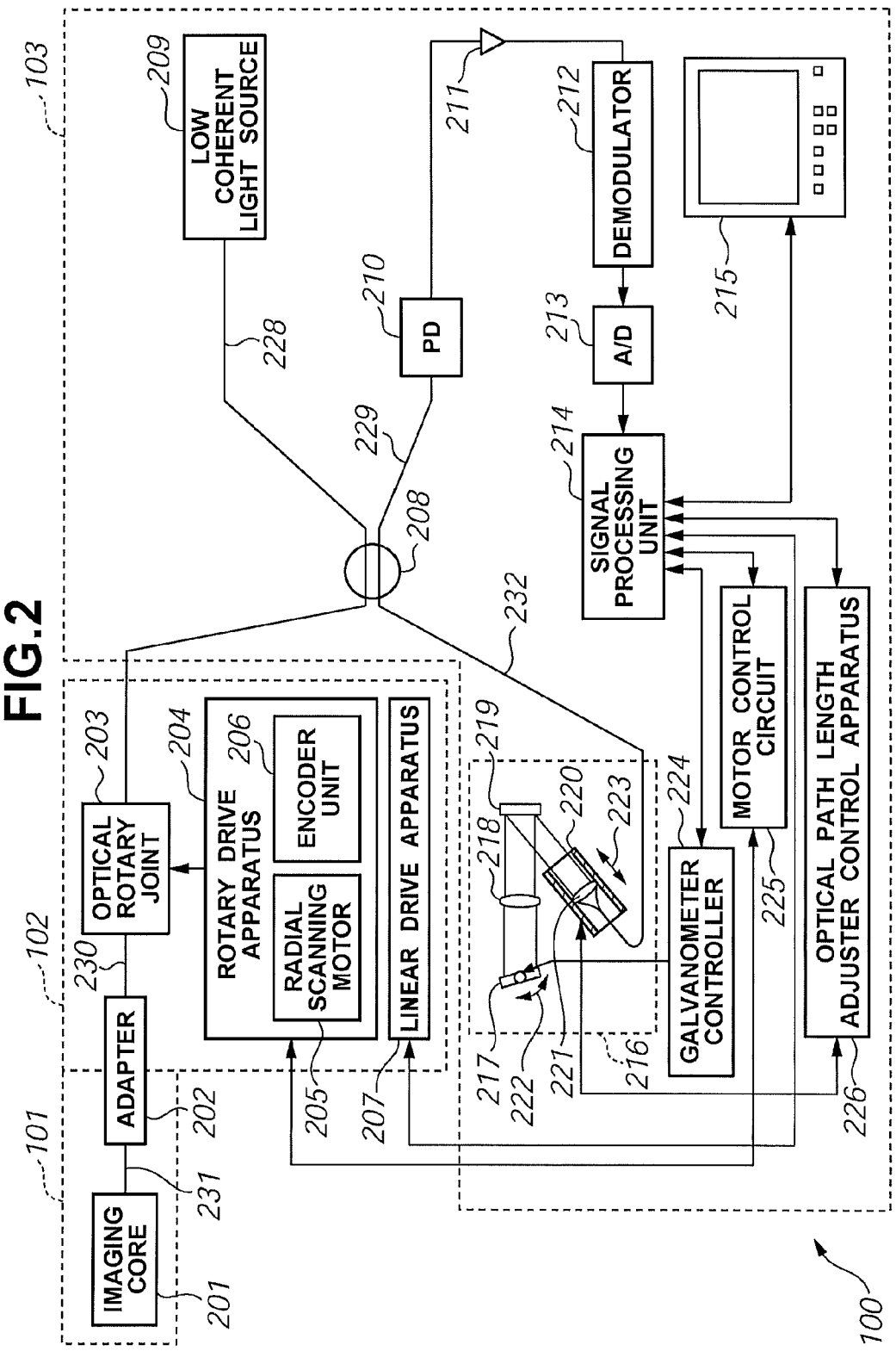
FIG. 2 is a block diagram of an example of an optical coherent tomography apparatus.

FIG. 2 illustrates aspects of the optical coherent tomography apparatus within the optical imaging diagnostic apparatus 100 relating to this embodiment disclosed by way of example.

A low coherent light source 209 of a super high intensity light-emitting diode or the like is provided. The low coherent light source 209 outputs a low coherent light whose wavelength is around 1310 nm and which shows coherence only in such a short distance range in which a coherent-able distance thereof (coherent length) is around a few μm to ten and a few μm.

Consequently, in a case in which this light is divided into two lights (two light paths) and the paths are thereafter mixed again, the light is to be detected as a coherent light in a case in which the difference between the two optical path lengths from a point at which the light is divided to a point at which they are mixed is within a short distance range of around a few μm to ten and a few μm or less, and light is not detected as a coherent light when the difference of the optical path lengths is larger than that.

The light of the low coherent light source 209 enters one end of a first single mode fiber 228 and is transmitted to the distal end surface side. The first single mode fiber 228 is connected optically with a second single mode fiber 229 and a third single mode fiber 232 by a photo coupler unit 208 on the way.

The photo coupler unit refers to an optical component in which it is possible to divide one optical signal into two or more outputs and/or to combine inputted two or more optical signals for one output and the light of the low coherent light source 209 is transmitted by being divided into three optical paths at the maximum by the photo coupler unit 208.

The scanner & pull-back unit 102 is provided on the distal end side ahead of the photo coupler unit 208 of the first single mode fiber 228. In the inside of a rotary drive apparatus 204 of the scanner & pull-back unit 102, there is provided an optical rotary joint 203 for connecting between a non-rotary portion (fixed portion) and a rotary portion (rotary drive portion) and for transmitting the light.

Further, the distal end side of a fourth single mode fiber 230 in the inside of the optical rotary joint 203 is connected freely detachably with a fifth single mode fiber 231 of the optical probe unit 101 through an adapter 202. Thus, the light from the low coherent light source 209 is transmitted to the fifth single mode fiber 231 which is passed-through in the imaging core 201 provided with the transmitting and receiving unit, which repeats the transmitting and receiving of the light and which is rotary-drivable.

The light transmitted to the fifth single mode fiber 231 is emitted while radially operating with respect to the biological tissue of the blood vessel from the transmitting and receiving unit arranged at the distal end of the imaging core 201. Then, a portion of the reflected light scattered on the surface or on the inside of the biological tissue is taken-in by the imaging core 201 and returns to the first single mode fiber 228 side through a reverse optical path, and a portion thereof moves to the second single mode fiber 229 side by the photo coupler unit 208. Then, it is light-received by a photo detector (for example, photo diode 210) owing to a fact that it is emitted from one end of the second single mode fiber 229.

The rotary drive portion side of the optical rotary joint 203 is rotatingly driven by a radial scanning motor 205 of the rotary drive apparatus 204. Also, a rotary angle of the radial scanning motor 205 is detected by an encoder unit 206. Further, the scanner & pull-back unit 102 is provided with a linear drive apparatus 207 and movement (axial-direction operation) in an axial direction (distal direction of the body lumen and opposite direction thereof) of the imaging core 201 is defined based on an instruction from a signal processing unit 214. The axial-direction operation is realized owing to the fact that the linear drive apparatus 207 makes the scanner including the optical rotary joint 203 move based on a control signal from the signal processing unit 214.

At that time, only the imaging core 201 inserted into a catheter sheath moves axially while the catheter sheath of the optical probe unit 101 is maintained to be fixed in the blood vessel, so that it is possible to carry out the axial-direction operation without injuring a blood vessel wall.

On the other hand, a variable mechanism 216 of the optical path length for changing the optical path length of the reference light is provided on the distal end side ahead the photo coupler unit 208 of the third single mode fiber 232 (on the reference light path).

The variable mechanism 216 of this optical path length is provided with a first optical path length changing unit for relatively speedily changing the optical path length which corresponds to an inspection region in the depth direction (direction of emission of the measurement light) of the biological tissue and a second optical path length changing unit for changing the optical path length which corresponds to fluctuation of the length thereof such that there can be absorbed the fluctuation of the length of the individual optical probe unit 101 in the case of using the optical probe unit 101 that has been exchanged.

Further, in the variable mechanism 216, facing the distal end of the third single mode fiber 232, there is arranged, through a collimating lens 221 which is freely movable in the direction shown in an arrow 223, with a mirror 219 which is mounted on an one-axis stage 220 together with this distal end. Also, there is mounted, through a mirror 218 corresponding to this mirror 219 (diffraction lattice), with a galvanometer 217 which is rotatable by a fine angle as the first optical path length changing unit. This galvanometer 217 is rotated relatively speedily in the direction of the arrow 222 by a galvanometer controller 224.

The galvanometer 217 is a device which reflects light by a mirror of the galvanometer and it is constructed such that the mirror mounted on a movable portion thereof is to be rotated relatively speedily by applying an AC drive signal to the galvanometer which functions as a reference mirror.

That is to say, owing to a fact that the drive signal is applied with respect to the galvanometer 217 from the galvanometer controller 224 and it is rotated fairly speedily by the drive signal in the direction of the arrow 222, the optical path length of the reference light changes relatively speedily only by the optical path length which corresponds to the inspection region in the depth direction of the biological tissue. One cycle of the change of this optical path difference becomes a cycle of obtaining coherent light for one line.

On the other hand, the one-axis stage 220 functions as the second optical path length changing unit having such an amount of variable range of optical path length, which can absorb the fluctuation of the optical path length of the optical probe unit 101 in case of exchanging the optical probe unit 101. Further, the one-axis stage 220 is also provided with a function as an adjuster for adjusting an offset. For example, even in a case in which the distal end of the optical probe unit 101 is not closely-attached to the surface of the biological tissue, it is possible, by changing the optical path length by the one-axis stage 220, to set it in a state of interfering with the reflected light from the surface position of the biological tissue.

The light whose optical path length is changed by the variable mechanism 216 of the optical path length is mixed with the reflected light obtained from the first single mode fiber 228 side by the photo coupler unit 208 which is provided on the way of the third single mode fiber 232 and is light-received as coherent light by the photo diode 210.

The coherent light which is light-received by the photo diode 210 in this manner is photoelectrically converted and amplified by an amplifier 211 and thereafter, is inputted to a demodulator 212.

In the demodulator 212, a demodulation process for extracting only the signal component of the coherent light is carried out and the output thereof is inputted to an A/D converter 213.

In the A/D converter 213, there is produced digital data "coherent light data" of one line by sampling the coherent light signal, for example, for 200 points. In this case, the sampling frequency becomes a value dividing one scanning time period of the optical path length by 200.

The coherent light data per line unit which is produced by the A/D converter 213 is inputted to a signal processing unit 214. In the signal processing unit 214, by carrying out a predetermined process with respect to the coherent light data, there is produced line data which are the coherent light intensity data in the depth direction of the biological tissue and thereafter, by converting the line data to the video signal, there is produces a cross-sectional image at each position in the axial direction inside the blood vessel, and it is outputted to a user interface apparatus 215 by a predetermined frame rate (corresponding to LCD monitor 113 and operation panel 112 in FIG. 1).

The signal processing unit 214 is connected further to an optical path length adjuster control apparatus 226. The signal processing unit 214 carries out the control of the position of the one-axis stage 220 through the optical path length adjuster control apparatus 226. Also, the signal processing unit 214 is connected to a motor control circuit 225 and controls the rotary drive of the radial scanning motor 205.

Further, the signal processing unit 214 is connected to the galvanometer controller 224 for controlling the scan of the optical path length of the reference mirror (galvanometer mirror) and the galvanometer controller 224 outputs the drive signal to the signal processing unit 214. In the motor control circuit 225, synchronization with the galvanometer controller 224 is taken by using this drive signal.

3. Construction of Optical Frequency Domain Imaging Apparatus Utilizing Wavelength Sweep Referring to FIG. 3, set forth below is a description of the construction and functional aspects of an optical frequency domain imaging apparatus utilizing wavelength sweep within the optical imaging diagnostic apparatus 100 according to one embodiment disclosed by way of example.

Figure 3:
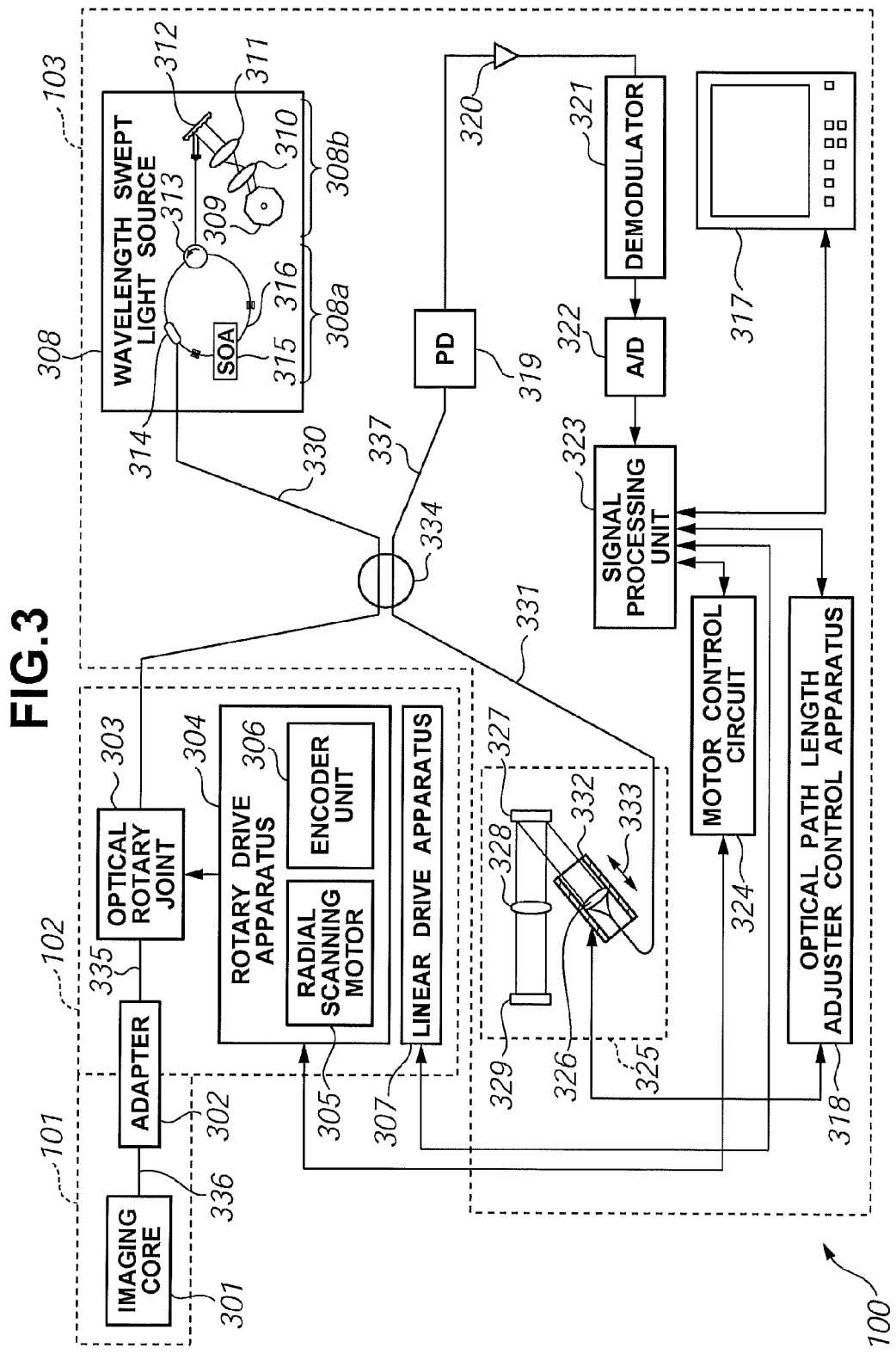
FIG. 3 is a block diagram of an example of an optical frequency domain imaging apparatus utilizing wavelength sweep.

Referring to FIG. 3, the optical frequency domain imaging apparatus 100 utilizing wavelength sweep includes a wavelength swept light source 308. In this embodiment, the wavelength swept light source 308 is a Swept-Laser. The wavelength swept light source 308 using the Swept-Laser is one kind of an Extended-Cavity-Laser which is composed of an optical fiber 316 connected with SOA315 (semiconductor optical amplifier) in a ring shape and a polygon scanning filter (308b).

The light outputted from the SOA315 proceeds inside the optical fiber 316 and enters the polygon scanning filter 308b and the wavelength selected here is amplified by the SOA315 and finally, it is outputted from a coupler 314.

In the polygon scanning filter 308b, the wavelength is selected depending on the combination of a diffraction lattice 312 for light-splitting the light and a polygon mirror 309. Specifically, the light which is light-split by the diffraction lattice 312 is focused on the surface of the polygon mirror 309 depending on two pieces of lenses (310, 311). Thus, it happens that only the light of the wavelength perpendicular to the polygon mirror 309 returns to the same optical path and is outputted from the polygon scanning filter 308b, so that it is possible to carry out the time sweep of the wavelength by rotating the polygon mirror 309.

For the polygon mirror 309, for example, an icosadodecahedron mirror is used and the rotation speed thereof is around 50000 rpm. Owing to the wavelength sweep system in which the polygon mirror 309 and the diffraction lattice 312 are combined, it becomes possible to employ the wavelength sweep of fairly high speed and high power.

The light of the wavelength swept light source 308, which is outputted from a coupler 314, enters one end of a first single mode fiber 330 and is transmitted to the distal end side. The first single mode fiber 330 is optically connected with a second single mode fiber 337 and a third single mode fiber 331 in a photo coupler unit 334 on the way. Therefore, the light which is entered into the first single mode fiber 330 is transmitted by being split into three optical paths at the maximum by this photo coupler unit 334.

On the distal end side ahead the photo coupler unit 334 of the first single mode fiber 330, there is provided, in a rotary drive apparatus 304, with an optical rotary joint 303 which connects between a non-rotary portion (fixed portion) and a rotary portion (rotary drive portion) and which transmits the light.

Further, the distal end side of a fourth single mode fiber 335 inside the optical rotary joint 303 is connected freely detachably through a fifth single mode fiber 336 and an adapter 302 of the optical probe unit 101. Thus, the light from the wavelength swept light source 308 is transmitted to the fifth single mode fiber 336 which is passed-through in an imaging core 301 and which is rotary-drivable.

The transmitted light is emitted from the transmitting and receiving unit arranged at a distal end of the imaging core 301 with respect to the biological tissue while being radially operated. Then, a portion of the reflected light which is scattered on the surface of or on the inside of the biological tissue is taken-in by the imaging core 301 and returns to the first single mode fiber 330 side through the reverse optical path. Further, the light is light-received by a photo detector (for example, photo diode 319) owing to a fact that a portion thereof moves to the second single mode fiber 337 side by the photo coupler unit 334 and is emitted from one end of the second single mode fiber 337.

The rotary drive portion side of the optical rotary joint 303 is rotatingly driven by a radial scanning motor 305 of the rotary drive apparatus 304. Also, rotary angle of the radial scanning motor 305 is detected by an encoder unit 306. Further, the scanner & pull-back unit 102 is provided with a linear drive apparatus 307 and defines the axial-direction operation of the imaging core 301 based on an instruction from a signal processing unit 323.

On the other hand, there is provided a variable mechanism 325 of the optical path length for fine-adjusting the optical path length of the reference light at a distal end on the opposite side with respect to the photo coupler unit 334 of the third single mode fiber 331.

The variable mechanism 325 of this optical path length is provided with the optical path length changing unit for changing the optical path length which corresponds to the fluctuation of the length thereof such that the fluctuation of the length of the individual optical probe unit 101 can be absorbed in case of using the optical probe unit 101 by being exchanged.

The third single mode fiber 331 and a collimating lens 326 are provided on a one-axis stage 332 which is freely movable in the optical axial direction thereof as shown by an arrow 333, and they form the optical path length changing unit.

Specifically, the one-axis stage 332 functions as the optical path length changing unit having such an amount of variable range of optical path length, which can absorb the fluctuation of the optical path length of the optical probe unit 101 in case of exchanging the optical probe unit 101. Further, the one-axis stage 332 is also provided with a function as an adjuster for adjusting an offset. For example, even in a case in which the distal end of the optical probe unit 101 is not closely-attached to the surface of the biological tissue, it becomes possible, by changing the optical path length by the one-axis stage, to set it in a state of interfering with the reflected light from the surface position of the biological tissue.

The light whose optical path length is fine-adjusted by the variable mechanism 325 of the optical path length is mixed with the reflected light obtained from the first single mode fiber 330 side by the photo coupler unit 334 which is provided on the way of the third single mode fiber 331 and is light-received by the photo diode 319.

The coherent light which is light-received by the photo diode 319 in this manner is photoelectrically converted and amplified by an amplifier 320 and thereafter, is inputted to a demodulator 321. In the demodulator 321, a demodulation process for extracting only the signal component of the coherent light is carried out and the output thereof is inputted to an A/D converter 322 as the coherent light signal.

In the A/D converter 322, there is produced digital data "coherent light data" of one line by sampling the coherent light signal, for example, for 2048 points by 180 MHz. The sampling frequency is set to be 180 MHz based on the assumption that about 90% of the cycle (12.5 μsec) of the wavelength sweep is to be extracted as the digital data of 2048 points in case of setting the repeat frequency of the wavelength sweep to be 80 kHz. The apparatus and method here are not limited in this respect.

The coherent light data per line unit produced in the A/D converter 322 is inputted to the signal processing unit 323. In the signal processing unit 323, the coherent light data are frequency-decomposed depending on an FFT (Fast Fourier Transform) and then, there are generated line data which are the coherent light intensity data in the depth direction, and by coordinate-converting those data, there is formed a cross-sectional image at each position in the axial direction of the inside of the blood vessel and it is outputted to an user interface apparatus 317 (which corresponds to LCD monitor 113 and operation panel 112 in FIG. 1) by a predetermined frame rate.

The signal processing unit 323 is connected further to an optical path length adjuster control apparatus 318. The signal processing unit 323 carries out the control of the position of the one-axis stage 332 through the optical path length adjuster control apparatus 318. Also, the signal processing unit 323 is connected to a motor control circuit 324 and receives a video synchronization signal of the motor control circuit 324. In the signal processing unit 323, the generation of the cross-sectional image is carried out in synchronization with the received video synchronization signal.

In addition, the video synchronization signal of this motor control circuit 324 is transmitted also to the rotary drive apparatus 304 and in the rotary drive apparatus 304, the drive signal in synchronization with the video synchronization signal is outputted.

Figure 4:
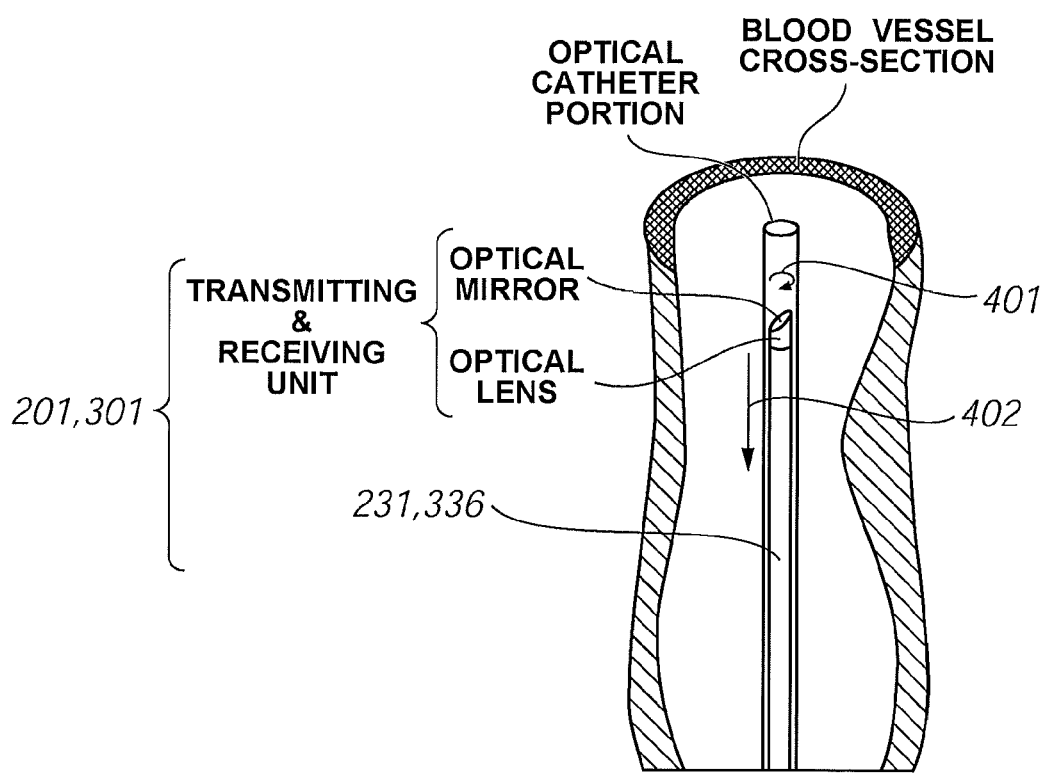
FIG. 4 is cross-sectional perspective view illustrating an imaging core distal end inserted into an optical probe unit of an optical imaging diagnostic apparatus and illustrating an operation of an imaging core in a state of being inserted into a blood vessel.

4. Construction of Distal End of Imaging Core Inserted in Optical Probe Unit and Operation of the Imaging Core Set forth below with reference to FIG. 4 is a description of the construction of a distal end of the imaging core 201, 301 inserted in the optical probe unit 101 and the operation of the imaging core 201, 301. FIG. 4 illustrates the construction of a distal end of the imaging core 201, 301 inserted in the optical probe unit 101, with the optical probe unit 101 inserted into a blood vessel.

As shown in FIG. 4, the imaging core 201, 301 provided with the transmitting and receiving unit and the optical fiber 231, 336 is inserted in the optical probe unit 101, and it is constructed to operate linearly in the direction of the arrow 402 while rotating in the direction of the arrow 401 inside the optical probe unit 101 which is inserted into the blood vessel (it is constructed to carry out radial operation).

The transmitting and receiving unit is provided with an optical mirror and an optical lens and emits the measurement light which is transmitted through the optical fiber 231, 336 in the direction approximately perpendicular to the axial direction (radial direction of the blood vessel). Also, the reflected light from the biological tissue with respect to the emitted measurement light is light-received and is transmitted to the steering control apparatus 103 side through the optical fiber 231, 336. Because the transmitting and receiving of such a light caused by the optical mirror and the optical lens is carried out during the radial operation of the imaging core 201, 301, it is possible to generate the line data necessary for drawing out a plurality of cross-sectional images inside the blood vessel in the axial direction.

Figure 5A:
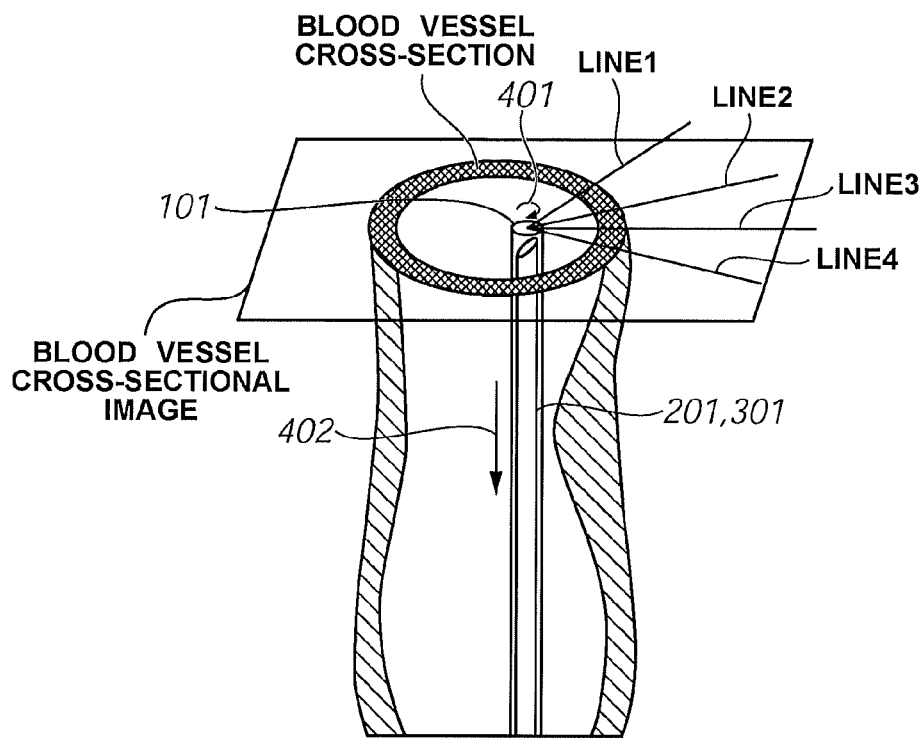
FIGS. 5A and 5B are cross-sectional perspective views illustrating an imaging core operation at the time of measurement in an optical imaging diagnostic apparatus and a generation process of a blood vessel cross-sectional image.

FIG. 5A is a diagram showing a state in which the measurement light is emitted toward the radial direction of the blood vessel while radially operating the imaging core 201, 301. As shown in FIG. 5A, because the measurement light is emitted while rotating the imaging core 201, 301 in the direction of the arrow 401, it is possible to light-receive the reflected light from the biological tissue at each position in the circumferential direction (that is, line data at each position can be generated). "Line 1", "Line 2", . . . shown in FIG. 5A express the distribution of the data which are generated based on the reflected light from the biological tissue of the measurement light which is emitted with respect to the biological tissue at each position in the circumferential direction. In this manner, owing to a fact that the line data of a plurality of lines are generated at each position in the axial direction, it is possible to draw out or generate the blood vessel cross-sectional image at each position in the axial direction.

Figure 5B:
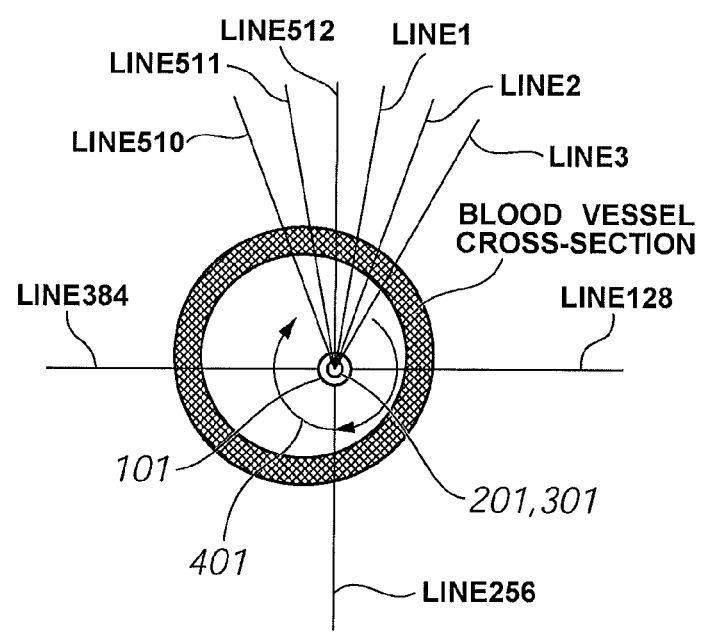

FIG. 5B is a diagram showing one example of the number of times of the measurement-light emissions toward the radial direction of the blood vessel at a predetermined position in the axial direction. In the example of FIG. 5B, 512-times emissions are carried out while the imaging core 201, 301 is rotated once in the circumferential direction and the line data for 512 lines are generated.

5. Features and Operational Aspects of Signal Processing Unit

Figure 6:
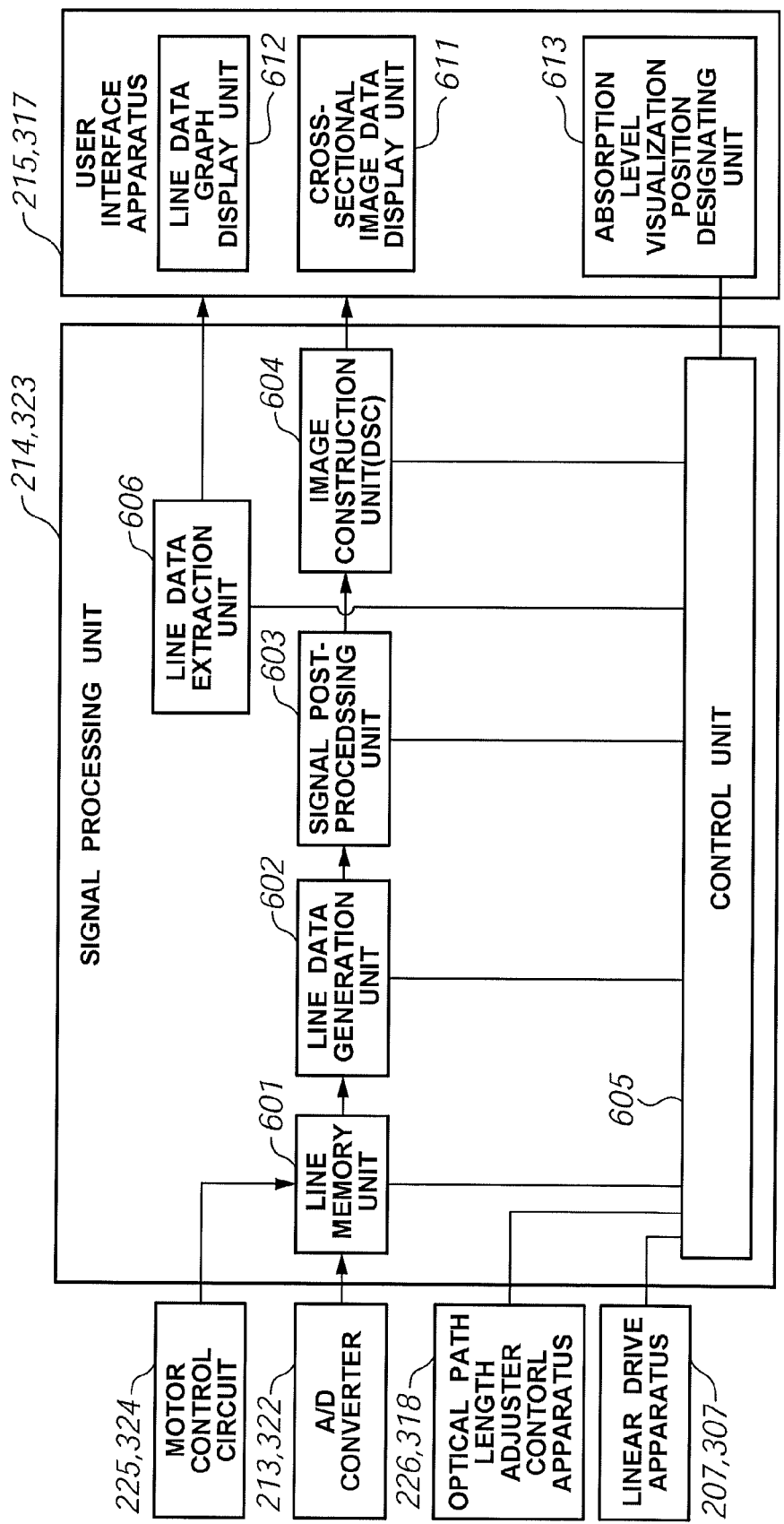
FIG. 6 is a diagram explaining the features and other functional aspects of a signal processing unit in an optical imaging diagnostic apparatus.

Referring to FIG. 6, set forth below is a discussion of the signal processing unit 214, 323 of the optical imaging diagnostic apparatus 100, including a description of operational aspects associated with the cross-sectional image developing or generating process for generating or developing the blood vessel cross-sectional image, and a visualization process for visualizing the absorption level of a predetermined biological tissue in the blood vessel cross-sectional image. It is possible for the cross-sectional image developing process and the visualization process explained below to be realized using a hardware for exclusive use or it is also allowed for the function of each portion to be realized by software (by executing a computer program).

FIG. 6 schematically illustrates features of the signal processing unit 214, 323 of the imaging diagnostic apparatus 100 used to perform the cross-sectional image generation process and the visualization process for visualizing the absorption level of a predetermined biological tissue in the blood vessel cross-sectional image. For purposes of simplifying the explanation, the description which follows focuses on the signal processing unit 214 of the optical coherent tomography apparatus 100 (in FIG. 2). Similar features and operational characteristics are used with an optical frequency domain imaging apparatus utilizing the wavelength sweep, and so a detailed discussion of the use in the context of an optical frequency domain imaging apparatus utilizing the wavelength sweep is not repeated here.

The coherent light data produced by the A/D converter 213 is processed in the line memory unit 601 such that the number of lines per one rotation of the radial scanning motor is 512 lines by using the signal of the encoder unit 206 of the radial scanning motor 205, which is outputted from the motor control circuit 225 and thereafter, it is outputted to the line data generation unit 602 in the succeeding stage.

In the line data generation unit 602, a line addition-averaging process, a filtering process, a logarithmic conversion process and the like are applied with respect to the coherent light data and the line data which is the coherent light intensity data in the depth direction of the biological tissue is generated and thereafter, the generated line data are outputted to the signal post-processing unit 603 in the succeeding stage. In the signal post-processing unit 603, a contrast adjustment, an intensity adjustment, a gamma correction, a frame correlation, a sharpness process and the like are carried out with respect to the line data and it is outputted to the image construction unit (DSC) 604.

In the image construction unit 604, a blood vessel cross-sectional image is generated owing to the fact that the line data series of the polar coordinate are Rθ-converted and thereafter, the image is converted to a video signal and the blood vessel cross-sectional image is displayed on the cross-sectional image data display unit (display) 611 of the user interface apparatus 215. In this embodiment disclosed as one example, the blood vessel cross-sectional image is generated from 512 lines, but the apparatus and method are not limited in this regard. The images(s) and information displayed on the display 611 is controlled by the control unit 605 which is an example of a display control means for controlling the display 611 to display the images(s) and other information as disclosed here.

The explanation set forth above is explained by assuming that the signal post-processing unit 603 directly processes the line data outputted from the line data generation unit 602, but the apparatus and method here are not limited in this respect as it is also possible to be constructed such that the line data outputted from the line data generation unit 602 is parallelly stored in a storage unit as a file form in association with predetermined patient attribute information and measurement condition information. In this case, it becomes in a state in which the signal post-processing unit 603 carries out the process described above by reading-out the line data from the storage unit based on an instruction of a user. It is possible for the storage unit to be provided inside the control unit 605 or to be provided outside the signal processing unit 214 (for example, it is also possible for the DVD recorder 111-1 to function as the storage unit). Alternatively, the line data generation unit 602 itself can serve as the storage unit.

There is provided in the user interface apparatus 215 an absorption level visualization position designating unit 613 constructed such that a position (predetermined circumferential-direction position in the circumference of the transmitting and receiving unit) at which there exists a biological tissue whose absorption level is assumed to be comprehended within the biological tissues constituting the blood vessel cross-sectional image displayed on the cross-sectional image data display unit 611 is to be designated on the blood vessel cross-sectional image. The absorption level visualization position designating unit 613 is an example of a designating means for designating a predetermined circumferential-direction position at the circumference of the transmitting and receiving unit on the cross-sectional image displayed Information relating to the position designated by the absorption level visualization position designating unit 613 is inputted to the control unit 605 and is transmitted to the line data extraction unit 606. In the line data extraction unit 606, the line data corresponding to the position designated by the absorption level visualization position designating unit 613, which are within the line data, are extracted from the storage unit. The line data extraction unit 606 is an example of an extraction means for extracting, from a storage unit and from amongst a plurality of the line data used to generate the cross-sectional image, the line data corresponding to the circumferential-direction position designated by the absorption level visualization position designating unit 613.

In the line data extraction unit 606, the line data extracted from the storage unit is displayed on the line data graph display unit 612 of the user interface apparatus 215 and concurrently, the attenuation rate of a predetermined range of the coherent light intensity in the emission direction (radial direction of the blood vessel) of the measurement light is calculated and is displayed in association with the line data. The description below will describe details of the visualization process from the position designation by the absorption level visualization position designating unit 613 until reaching the display of the corresponding line data and the calculation of the attenuation rate.

6. Visualization Process for Visualizing Absorption Level

Figure 7:
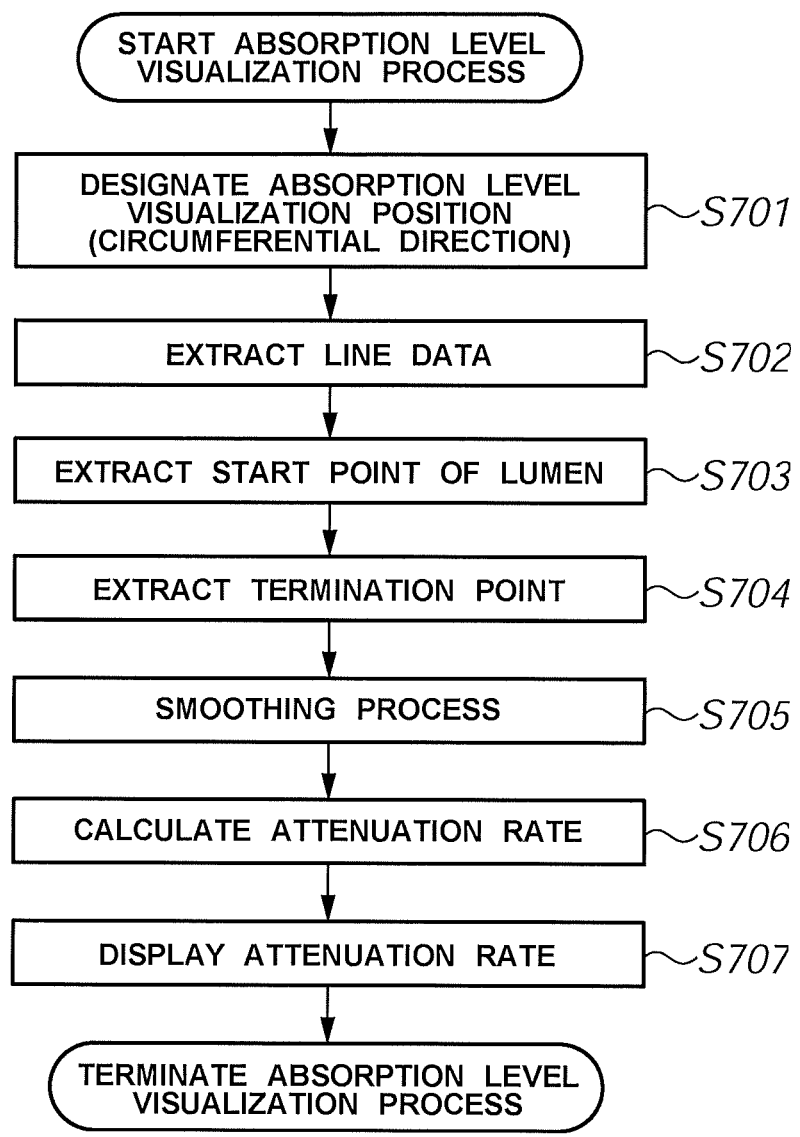
FIG. 7 is a flowchart showing an absorption level visualization process for visualizing absorption level of a predetermined biological tissue based on a blood vessel cross-sectional image.
Figure 8A:
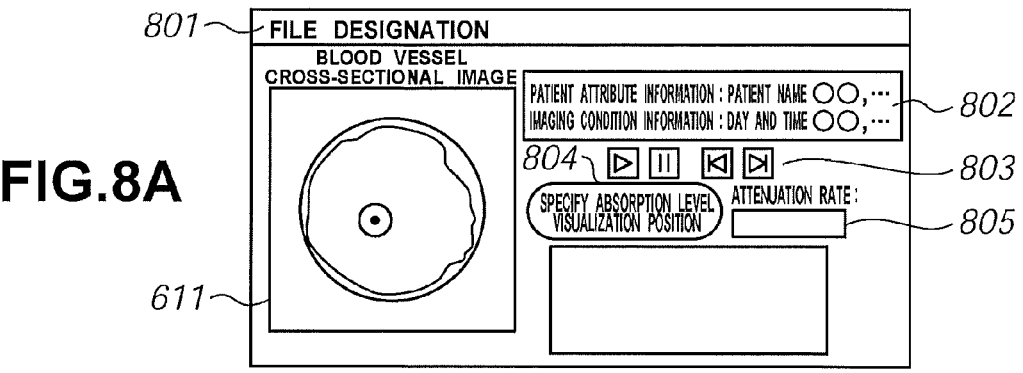
FIGS. 8A-8D are diagrams showing an example of a user interface used for a steering when visualizing absorption level of a predetermined biological tissue based on a drawn-out blood vessel cross-sectional image.
Figure 8B:
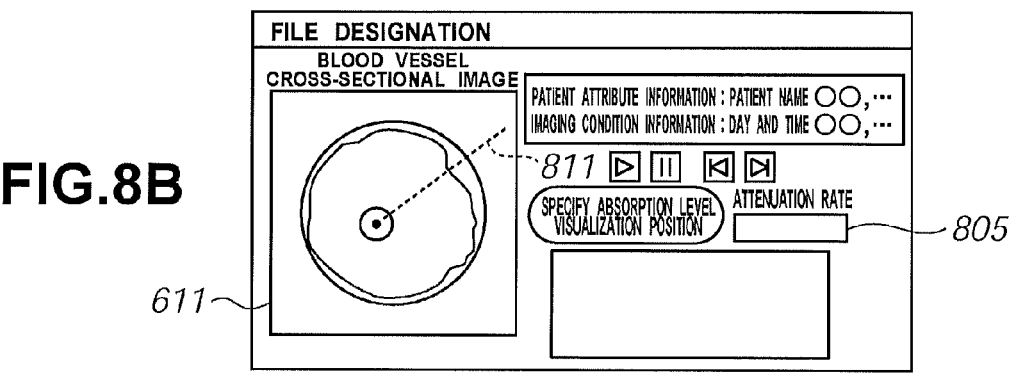
Figure 8C:
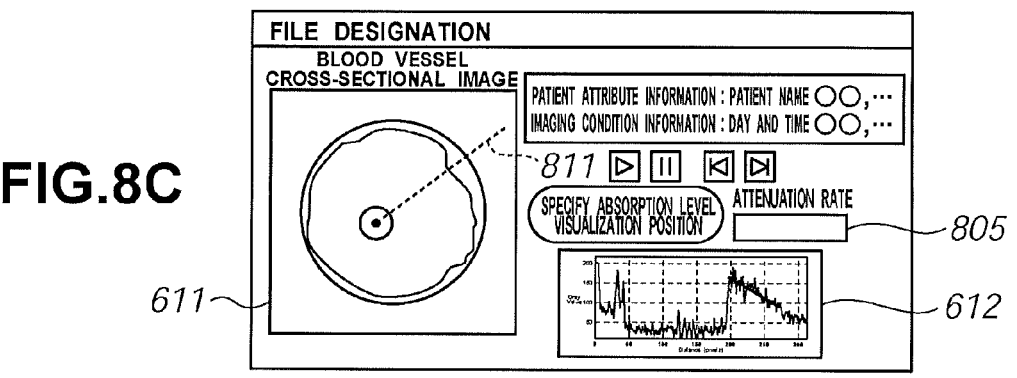
Figure 8D:
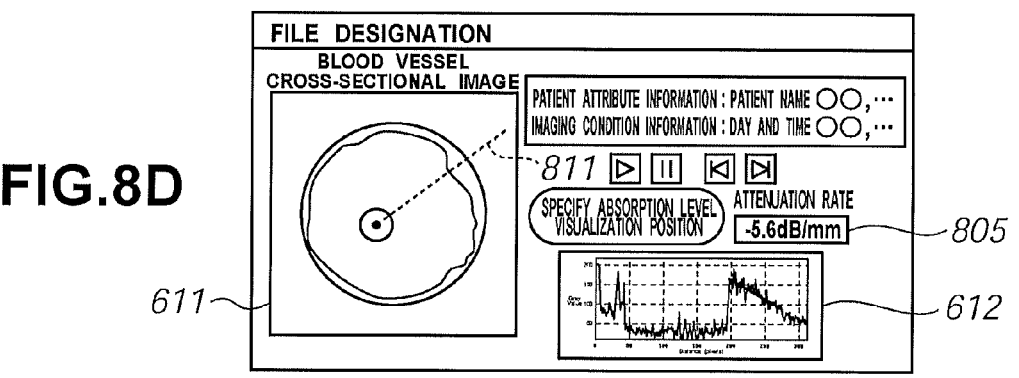
Figure 9:
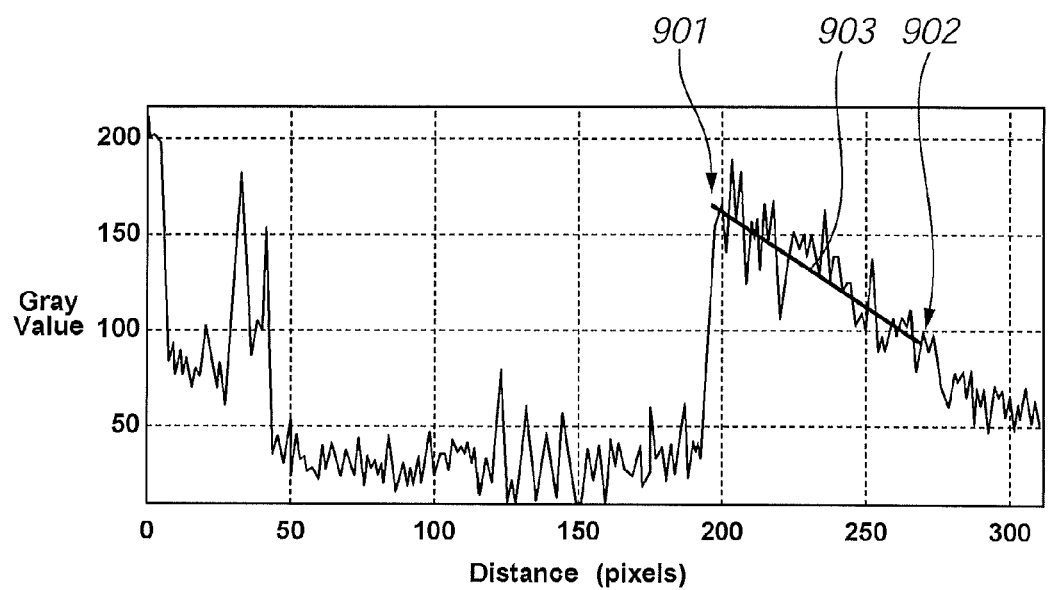
FIG. 9 is one example of a graph in which absorption level of a predetermined tissue is visualized.

Referring to FIGS. 7-9, the description which follows describes the visualization process for visualizing the absorption level of each biological tissue constituting the blood vessel cross-sectional image.

As shown in FIG. 8A, in the user interface used when visualizing the absorption level, there is arranged a file-designation button 801 for designating a desired file from a plurality of files in which line data for generating the blood vessel cross-sectional image are stored. Also, there are arranged a cross-sectional image data display unit 611 for displaying the blood vessel cross-sectional image continuously in real time at the time of measurement (or for displaying the blood vessel cross-sectional image continuously based on the line data stored in the designated file) and a display area 802 for displaying various kinds of information (patient attribute information showing the attribute of a patient such as a patient name, and measurement condition information such as a measurement day and time, and the settings at the time of measurement) with respect to the blood vessel cross-sectional image which is displayed on the cross-sectional image data display unit 611.

Further, the cross-sectional image data display unit 611 is provided with an operation switch 803 for displaying a plurality of blood vessel cross-sectional images continuously, for temporarily-stopping the blood vessel cross-sectional image which is displayed continuously, for fast-forwarding or rewinding the display and the like.

With this construction, a user operates, for example, the file-designation button 801 and reads-out a desired file and concurrently, makes the blood vessel cross-sectional image of the desired position in the axial direction be displayed on the cross-sectional image data display unit 611 by operating an operation switch 803. When the operation is completed by a user, the absorption level visualization process shown in FIG. 7 is started. The absorption level visualization process shown in FIG. 7 is carried out by the control unit 605 which controls the various aspects of the routine.

When the absorption level visualization process is started, in step S701, the absorption level visualization position designating unit 613 accepts the designation of the absorption level visualization position. Specifically, when a user presses an absorption level calculation position-designation switch 804 in FIG. 8A, as shown in FIG. 8B, a designation line 811 is displayed on the cross-sectional image data display unit 611. The designation line 811 is a line extending in the radial direction of the blood vessel by setting the center position of the transmitting and receiving unit of the imaging core 201, 301 as an endpoint node, and it is constructed so as to be rotated in the circumferential direction depending on the steering by the user. Consequently, when a user moves another one of the endpoint nodes of the designation line 811 in the circumferential direction and matches it with the position of the biological tissue whose absorption level is desired to be known or comprehended, the designation of the absorption level visualization position can be carried out. In the signal processing unit 214, 323, the circumferential-direction position which is designated by the designation line 811 is accepted as the absorption level visualization position.

When the designation of the absorption level visualization position is accepted, in step S702, the line data extraction unit 606 extracts the line data corresponding to the position accepted in the step S701 from the storage unit which is not-shown and concurrently, displays the extracted line data on the line data graph display unit 612 (see FIG. 8C).

In step S703, to find out the attenuation curve in a predetermined region corresponding to a predetermined biological tissue within the line data extracted in step S702, a start point of the lumen is extracted from the extracted line data. Specifically, a differentiation process is carried out in the radial direction from a position corresponding to the outer surface of the catheter sheath of the optical probe unit 101, and the point at which the differentiation value is a predetermined threshold value (first predetermined threshold value) or more and also at which the scattering intensity (coherent light intensity) is a predetermined threshold value (second predetermined threshold value different from the first predetermined threshold value) or more is made to be a start point of the lumen.

In step S704, a termination point for finding out the attenuation curve is extracted. Specifically, a position which is at a predetermined distance (for example, 50 pixels) in the radial direction from the start point of the lumen extracted in step S703 is made to be the termination point.

A smoothing process is carried out in step S705 for smoothing the line data between the start point of the lumen extracted in step S703 and the termination point extracted in step S704. Specifically, the line data are smoothed by applying a movement averaging process and a median filtering process with respect to the line data between the start point and the termination point.

In step S706, with respect to the line data which is applied with the smoothing process, the attenuation rate of the coherent light intensity is found out between the start point and the termination point by using, for example, a least squares method or the like. The control unit 605 (FIG. 6) which carries out the operational sequence shown in FIG. 7 is thus an example of a calculation means which calculates the attenuation rate in a predetermined region in the radial direction of the body lumen with respect to the extracted line data. In step S707, the calculated attenuation rate is displayed on the user interface apparatus 317 (see 805 of FIG. 8D) and concurrently, the calculated attenuation curve is displayed by being superimposed on the line data which are displayed on the line data graph display unit 612 (see 612 of FIG. 8D). Thus, the attenuation rate and the attenuation curve which are calculated are displayed in association with the blood vessel cross-sectional image and the designation line 811.

FIG. 9 is an enlarged view showing the line data which is displayed on the line data graph display unit 612 and the attenuation curve which is displayed by being superimposed on the line data. As shown in FIG. 9, on the line data graph display unit 612, there are displayed the distance in the radial direction (distance in the radial direction of the blood vessel in which the optical lens is the start point) in the horizontal axis and the intensity value in the vertical axis.

In an example of FIG. 9, there is shown a state in which an attenuation curve 903 determined according to the least squares method is superimposed on the line data by setting a reference numeral 901 to be the start point and a reference numeral 902 to be the termination point. It is possible for a user to comprehend high and low levels in the absorption level based on the inclination of the attenuation curve 903 (in a case in which the inclination of the attenuation curve 903 is large, it is possible to recognize that the absorption level of the biological tissue at the position is high and in a case in which the inclination of the attenuation curve 903 is small, it is possible to recognize that the absorption level of the biological tissue at the position is low).

In this manner, by visualizing the absorption level in the biological tissue and by making it possible to recognize it quantitatively, it becomes possible for a user to identify the biological tissue based on the difference of the absorption level.

As is understood from the explanation above, in the optical imaging diagnostic apparatus relating to this embodiment disclosed by way of example, a construction is employed in which it is possible, on the displayed blood vessel cross-sectional image, for a user to optionally designate the biological tissue whose absorption level is to be known or comprehended.

Also, in a case in which there is designation from a user, there is employed a construction in which the line data corresponding to the position is extracted and displayed on the user interface apparatus and concurrently, the attenuation rate of a predetermined region is calculated based on the line data and is displayed. Thus, it is possible for a user to recognize high and low levels in the absorption level of the biological tissue at a desired position on the blood vessel cross-sectional image as large and small rates in the attenuation rate.

Further, there is employed a construction in which the start point and the termination point which are used for the calculation of the attenuation rate and the attenuation curve calculated depending on the least squares method are displayed by being superimposed on the line data. Thus, it is possible for a user to fairly easily recognize which region in the radial direction of the line data is targeted by the calculated attenuation rate and concurrently, it is possible to recognize the absorption level in such a fashion as the inclination of the attenuation curve.

Second Embodiment

In the first embodiment described above, on an occasion when calculating the attenuation curve, the point at which the differential value is a predetermined threshold value or more and also the scattering intensity (coherent light intensity) is a predetermined threshold value or more is set to be the start point. But the apparatus and method is not limited by this aspect and, for example, it is also possible for a point which is deviated as many as a few pixels from the point at which the differential value is a predetermined threshold value or more and also the scattering intensity (coherent light intensity) is a predetermined threshold value or more to be extracted as the start point. Thus, it becomes possible to repress the fluctuation of the numerical value caused by the reflection from the surface of the biological tissue and it becomes possible to calculate the attenuation rate accurately.

Also, in the first embodiment described above, when calculating the attenuation curve, a construction is employed in which the smoothing process is carried out preliminarily between the start point and the termination point, but the apparatus and method are not limited in this regard, and it is also possible to employ a construction in which the smoothing process is omitted.

In addition, in the first embodiment described above, it is assumed that the attenuation curve is calculated directly by using the extracted line data, but the apparatus and method here are not limited in this regard, and it is possible to employ an arrangement in which the attenuation curve is calculated after there is carried out the process for correcting the sensitivity difference resulting from the position (position in the axial direction, position in the circumferential direction or position in the radial direction) in the blood vessel cross-sectional image of the extracted line data. Specifically, it is possible to employ a construction in which the sensitivity curve corresponding to the position of the line data is prepared preliminarily and the extracted line data are subtracted from the corresponding sensitivity curve.

Third Embodiment

In the first embodiment described above, the attenuation rate is calculated with respect to the line data designated by the designation line, but the apparatus and method here are not limited in this regard as it is also possible to employ a arrangement in which the attenuation rate is calculated by targeting all of the circumferential directions (all line data used for generating the blood vessel cross-sectional image).

Also, it is also possible to display, in an emphasized manner, the position on the blood vessel cross-sectional image corresponding to the line data having the attenuation rate identical to that of the designated line data within the attenuation rates of all the calculated line data. To emphasize the display in such a case, the emphasis can be achieved in various ways such as colorization, thick-line, gray-out and others.

The detailed description above describes features and aspects of embodiments of an optical imaging diagnostic apparatus and a display control method. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An optical imaging diagnostic apparatus in which a probe includes an imaging core provided with a transmitting and receiving unit for carrying out continuous transmitting of light which is reflected from biological tissue and received as obtained reflected light by the transmitting and receiving unit, with the transmitting and receiving unit being axially movable inside a body lumen while also rotating the transmitting and receiving unit, to generate a plurality of cross-sectional images in an axial direction of the biological tissue using line data of coherent light produced by interference between the obtained reflected light and reference light, the apparatus comprising:
   a display which displays a first display area for displaying a cross-sectional image of the plurality of cross-sectional images and a second display area for displaying a calculated attenuation rate;
   a storage unit which stores a plurality of the line data including the line data used to generate the displayed cross-sectional image;
   a display control means for controlling the display to display, in the first display area, the cross-sectional image based on the line data stored in the storage unit and, superimposed on the displayed cross-sectional image, a line extending in a radial direction of the body lumen by setting a center position of the transmitting and receiving unit of the imaging core as an endpoint node;
   designating means for designating on the displayed cross-sectional image the radial direction of the line depending on steering by a user;
   extraction means for extracting, from amongst the plurality of the line data used to generate the cross-sectional image and which is stored in the storage unit, the line data corresponding to the radial direction designated by the designating means; and
   calculation means for calculating attenuation rate in a predetermined region in the radial direction of the body lumen with respect to the line data extracted by the extraction means;
   wherein the display control means controls the display to display, in the second display area, the attenuation rate calculated by the calculation means.

2. The optical imaging diagnostic apparatus according to claim 1, wherein the calculation means calculates the attenuation rate by setting a region, in which a point at which line data value is a predetermined threshold value or more and also at which a differential value in the radial direction of the line data becomes a predetermined threshold value or more is a start point, and a point at a predetermined distance in the radial direction from the start point is a termination point, to be the predetermined region.

3. The optical imaging diagnostic apparatus according to claim 1, wherein the calculation means calculates the attenuation rate by setting a region, in which a point at which line data value is a predetermined threshold value or more and also is spaced a predetermined distance in the radial direction from a point at which a differential value in the radial direction of the line data becomes a predetermined threshold value or more is made to be a start point, and a point of a further predetermined distance in the radial direction from the start point, is made to be a termination point, to be the predetermined region.

4. The optical imaging diagnostic apparatus according to claim 1, wherein the display displays, in a visually emphasized manner on the displayed cross-sectional image in the first display area, an area corresponding to the predetermined region of the line data having an attenuation rate equal to the attenuation rate calculated by the calculation means.

5. A display control method of an optical imaging diagnostic apparatus, the apparatus comprising a probe including an imaging core provided with a transmitting and receiving unit for carrying out continuous transmitting of light which is reflected from biological tissue and received as obtained reflected light by the transmitting and receiving unit, with the transmitting and receiving unit being axially movable inside a body lumen while also rotating the transmitting and receiving unit, to generate a plurality of cross-sectional images in an axial direction of the biological tissue using line data of coherent light produced by interference between the obtained reflected light and reference light, the method comprising:

displaying a first display area for displaying a cross-sectional image of the plurality of cross-sectional images and a second display area for displaying a calculated attenuation rate;

storing a plurality of the line data including the line data used to generate the displayed cross-sectional image;

displaying, in the first display area, the cross-sectional image based on the line data stored in the storage unit and, superimposed on the displayed cross-sectional image, a line extending in a radial direction of the body lumen by setting a center position of the transmitting and receiving unit of the imaging core as an endpoint node;

designating on the displayed cross-sectional image, the radial direction of the line depending on steering by a user;

extracting, from the line data used to generate the cross-sectional image, line data corresponding to the designated radial direction;

calculating an attenuation rate in a predetermined region in the radial direction of the body lumen with respect to the extracted line data; and displaying, in the second display area, the calculated attenuation rate.

6. The display control method according to claim 5, wherein the predetermined region comprises a region, in which a point at which line data value is a predetermined threshold value or more and also at which a differential value in the radial direction of the line data becomes a predetermined threshold value or more is a start point, and a point at a predetermined distance in the radial direction from the start point is a termination point.

7. The display control method according to claim 5, wherein the predetermined region comprises a region, in which a point at which line data value is a predetermined threshold value or more and also is spaced a predetermined distance in the radial direction from a point at which a differential value in the radial direction of the line data becomes a predetermined threshold value or more is made to be a start point, and a point of a further predetermined distance in the radial direction from the start point, is made to be a termination point.

* * * * *